(12) United States Patent
    Van Hende (10) Patent No.: US 8,712,684 B2
(45) Date of Patent: *Apr. 29, 2014

(54) METHOD OF CREATING EXERCISE ROUTES FOR A USER AND RELATED PERSONAL NAVIGATION DEVICE

(75) Inventor: Iwan Van Hende, Tao-Yuan Hsien (TW)

(73) Assignee: Mitac International Corp., Kuei-Shan Hsiang, Tao-Yuan Hsien (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/461,789

(22) Filed: May 2, 2012

(65) Prior Publication Data

US 2013/0297201 A1 Nov. 7, 2013

(51) Int. Cl.
    *G01C 21/34* (2006.01)
(52) U.S. Cl.
    USPC .......................................... 701/425; 701/426
(58) Field of Classification Search
    USPC ................................................ 701/425, 426
    See application file for complete search history.

(56) References Cited

U.S. PATENT DOCUMENTS

2001/0025222 A1* 9/2001 Bechtolsheim et al. ...... 701/209
2007/0156335 A1 7/2007 McBride
2008/0009275 A1 1/2008 Werner
2010/0088023 A1* 4/2010 Werner .......................... 701/206
2012/0101717 A1 4/2012 Zhang

FOREIGN PATENT DOCUMENTS

EP 2 172 249 A2 4/2010
EP 2 172 249 A3 9/2010

OTHER PUBLICATIONS

Van Hende, Title of Invention: Method of creating varied exercise routes for a user, U.S. Appl. No. 13/467,051, filed May 9, 2012.

* cited by examiner

*Primary Examiner* — Mary Cheung
*Assistant Examiner* — Yuen Wong
(74) *Attorney, Agent, or Firm* — Winston Hsu; Scott Margo (57) ABSTRACT

A method of creating an exercise route for a user of a personal navigation device includes receiving a selection of a length of an exercise route to be generated, and generating a first plurality of suggested exercise routes according to a current position of the personal navigation device and the selected length of the exercise route, where each of the first plurality of suggested exercise routes has a starting point and ending point substantially equal to one another and equal to the current position of the personal navigation device. The method further includes displaying the first plurality of suggested exercise routes to the user on a display of the personal navigation device, receiving, from the user, selection of a selected suggested exercise route from the first plurality of suggested exercise routes, and displaying routing instructions on the display of the personal navigation device for the selected suggested exercise route.

24 Claims, 7 Drawing Sheets

METHOD OF CREATING EXERCISE ROUTES FOR A USER AND RELATED PERSONAL NAVIGATION DEVICE

BACKGROUND OF THE INVENTION

1. Field of the Invention

The invention relates to a personal navigation device, and more particularly, to a personal navigation device that automatically creates a plurality of suggested exercise routes for the user to select from.

2. Description of the Prior Art

Global Positioning System (GPS) based navigation devices are well known and are widely employed as in-car navigation devices. Common functions of a navigation device include providing a map database for generating navigation instructions that are then shown on a display of the navigation device. These navigation devices are often mounted on or in the dashboard of a vehicle using a suction mount or other mounting means.

The term "navigation device" refers to a device that enables a user to navigate to a pre-defined destination. The device may have an internal system for receiving location data, such as a GPS receiver, or may merely be connectable to a receiver that can receive location data. The device may compute a route itself, or communicate with a remote server that computes the route and provides navigation information to the device, or a hybrid device in which the device itself and a remote server both play a role in the route computation process. Portable GPS navigation devices are not permanently integrated into a vehicle but instead are devices that can readily be mounted in or otherwise used inside a vehicle. Generally (but not necessarily), they are fully self-contained—i.e. include an internal GPS antenna, navigation software and maps and can hence plot and display a route to be taken.

Currently, personal navigation devices used for outdoor activities such as hiking, jogging, or cycling are limited in their options presented to users. Route planning with conventional personal navigation devices is performed by the user entering a starting point, an ending point, and possibly a waypoint, with the personal navigation devices creating a planned route for the user based on these criteria. However, this requires the user to enter these locations manually, which requires extra time from the user that could instead be spent exercising.

Unlike when driving a vehicle, when exercising, the user is not usually interested in merely getting from point A to point B as quickly as possible. Unfortunately, when creating a route between point A and point B, conventional personal navigation devices always provide the same route and do not offer any alternatives. Thus, the user may get tired of exercising on the same route every time. Furthermore, sports-based personal navigation devices do not always provide any personalized routes based on specific user requirements or existing training programs followed by the user.

SUMMARY OF THE INVENTION

It is therefore one of the primary objectives of the claimed invention to provide a method of creating a plurality of suggested exercise routes for the user to select from in order to provide a more enjoyable and varied exercise experience.

According to an exemplary embodiment of the claimed invention, a method of creating an exercise route for a user of a personal navigation device is disclosed. The method includes storing a database in a memory of the personal navigation device, the database comprising geographic data, receiving a selection of a length of an exercise route to be generated, and generating a first plurality of suggested exercise routes according to a current position of the personal navigation device and the selected length of the exercise route, wherein each of the first plurality of suggested exercise routes has a starting point and ending point substantially equal to one another and equal to the current position of the personal navigation device. The method further includes displaying the first plurality of suggested exercise routes to the user on a display of the personal navigation device, receiving, from the user, selection of a selected suggested exercise route from the first plurality of suggested exercise routes, and displaying routing instructions on the display of the personal navigation device for the selected suggested exercise route.

According to another exemplary embodiment of the claimed invention, a personal navigation device for creating an exercise route for a user of the personal navigation device is disclosed. The personal navigation device includes a memory storing a database comprising geographic data, a user interface for receiving from the user a selection of a length of an exercise route to be generated, and routing software for generating a first plurality of suggested exercise routes according to a current position of the personal navigation device and the selected length of the exercise route, wherein each of the first plurality of suggested exercise routes has a starting point and ending point substantially equal to one another and equal to the current position of the personal navigation device. The personal navigation device further comprises a processor for controlling a display of the personal navigation device to display the first plurality of suggested exercise routes to the user, and for controlling the display to display routing instructions for a selected suggested exercise route in response to the user interface receiving from the user selection of the selected suggested exercise route from the first plurality of suggested exercise routes.

It is an advantage that the present invention method automatically creates a plurality of suggested exercise routes for the user to select from in order to provide a more enjoyable and varied exercise experience for the user. The plurality of suggested exercise routes are automatically created for the user based on the user's current location and the length of the exercise route specified by the user. In this way, the user does not need to manually create an exercise route, thereby saving time in planning a route. Further, the user can either select one of the plurality of suggested exercise routes, or the user can request generation of another plurality of suggested exercise routes to choose from. As a result, the user can exercise on an unlimited number of exercise routes that are enjoyable and challenging, making it more likely that the user will continue exercising for improving fitness. The present invention will always create different routes so the user can enjoy endless possibilities of exercising.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
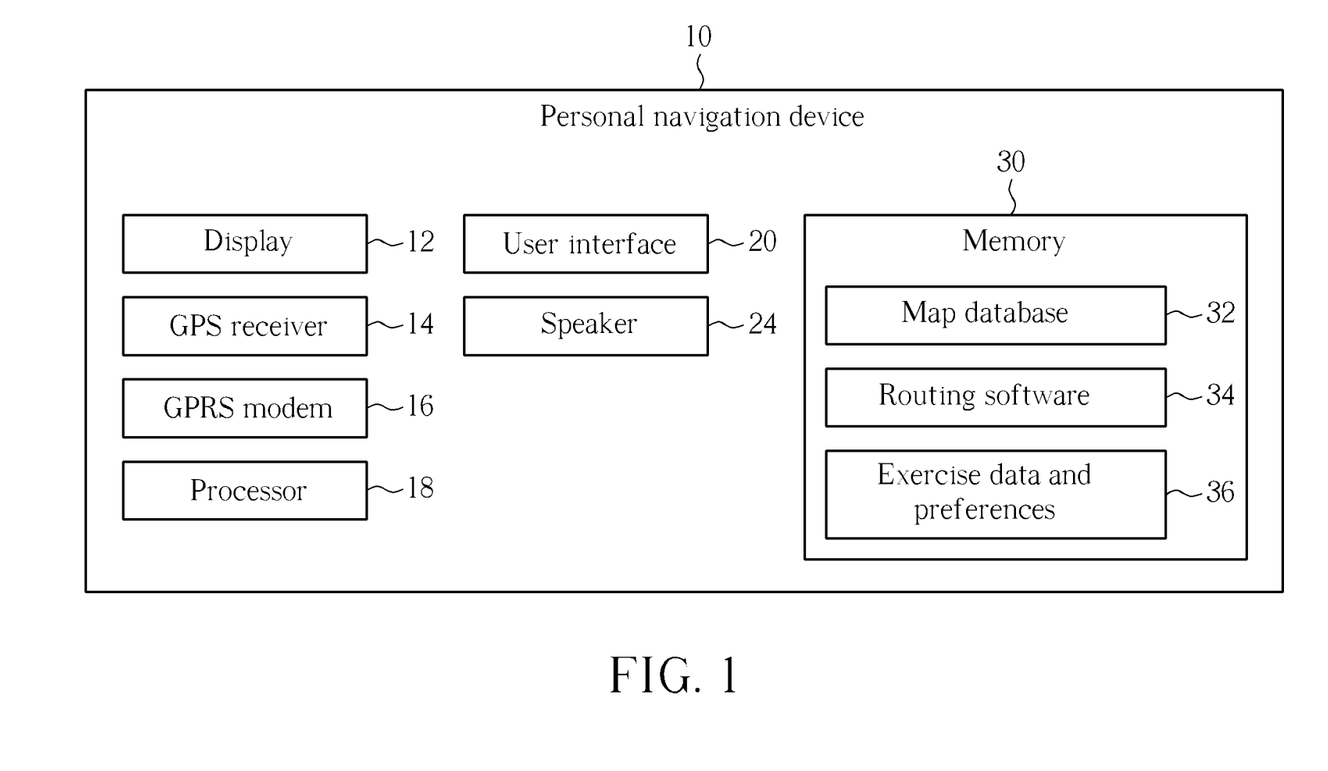
FIG. 1 is a block diagram of a personal navigation device according to the present invention.

Please refer to FIG. 1. FIG. 1 is a block diagram of a personal navigation device 10 according to the present invention. The personal navigation device 10 contains a display 12 which can be a touch sensitive display, a GPS receiver 14 for receiving the current position coordinates of the personal navigation device 10, a General Packet Radio Service (GPRS) modem 16 for providing internet access and data connectivity, a processor 18 for controlling operation of the personal navigation device 10, a user interface 20, a speaker 24 for outputting audio instructions to the user, and a memory 30. Instead of the speaker 24, a buzzer can also be used to provide audio feedback to the user. The memory 30 is used to store a map database 32 containing map data and points of interest. The memory 30 also stores routing software 34 used to create routes for the user to follow. User data such as exercise data and preferences 36 is also stored in the memory 30 in order to have a record of what training level the user is at and what length of exercise routes the user prefers. Description of the GPRS modem 16 is not intended to limit the scope of the present invention, and any wireless modem that can connect to the Internet can be used instead of the GPRS modem 16. Other connectivity options besides the GPRS modem that can be used for data transfer include communication according to the ANT+, Wi-Fi, 3G, or Bluetooth protocols. The personal navigation device 10 can also be provided with a camera for allowing the user to take geotagged photographs and to share them with others.

A distinguishing feature of the present invention is the use of a "Surprise me" function for surprising the user with automatically generated suggested exercise routes. The user simply needs to indicate the length of the exercise route desired and the routing software 34 of the personal navigation device 10 will automatically generate multiple suggested exercise routes for the user to select from. Once the user selects one of the suggested exercise routes, the routing software 34 prepares navigation instructions for the user to follow the selected exercise route.

Figure 2:
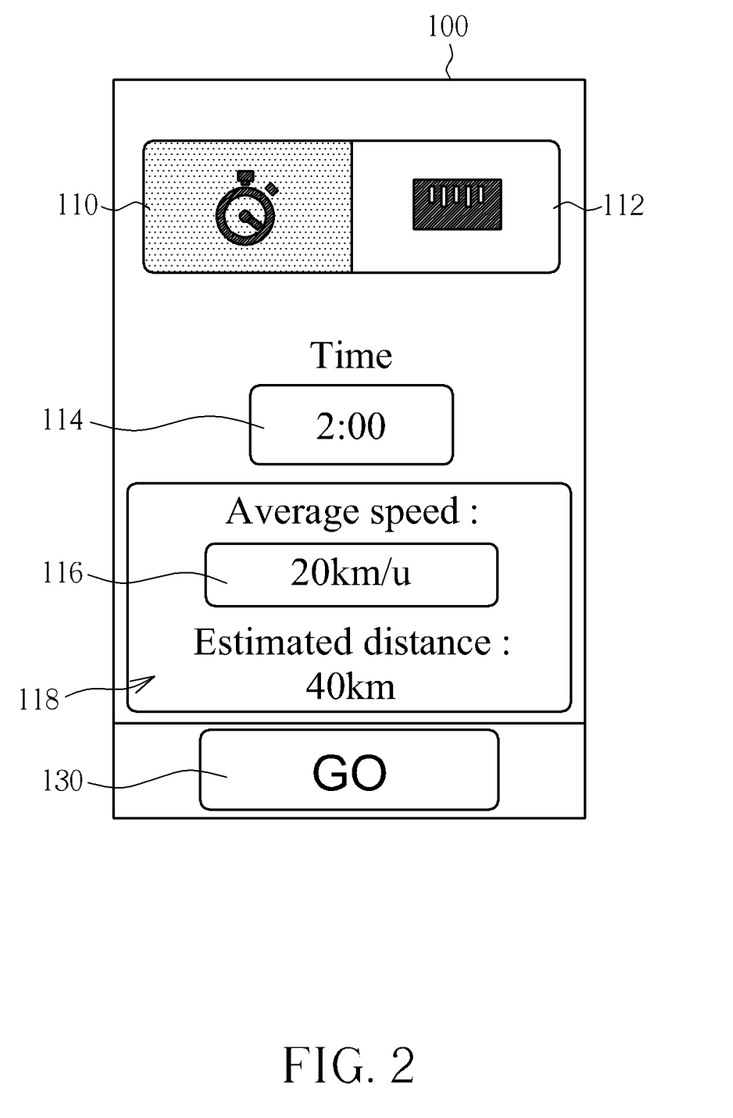
FIG. 2 is a screen showing settings for creating suggested exercise routes with the surprise me function using a combination of exercise time and average speed at which the user will move while exercising.

Please refer to FIG. 2. FIG. 2 is a screen 100 showing settings for creating suggested exercise routes with the surprise me function using a combination of exercise time and average speed at which the user will move while exercising. The screen 100 shown in FIG. 2 is a simplified example in which only the exercise time and average speed are entered by the user. Other parameters can be specified by the user instead, and the user can specify one or more of time, distance, waypoints to be visited on the exercise route, a direction of a city that the route should head towards, a wind direction to use or avoid, a difficulty level of the exercise route in terms of how flat or steep the exercise route is, heart rate to be achieved by the user on the exercise route, calories to be burned by the user on the exercise route, an expected height or an expected elevation gain of the exercise route, preferred points of interest to be visited on the exercise route, starting and ending points that are different from one other, an unspecified ending point being a specific distance away from the starting point, and surface types such as paved, unpaved, cobblestones, etc. As shown on the screen 100, the user has selected a time button 110 for indicating the route length in terms of an entered exercise time 114 and entered average speed 116. The entered average speed 116 can be automatically filled in for the user based on the user's history of average speeds or the user can manually change the entered average speed 116 to a different value. For instance, the entered exercise time 114 shown in FIG. 2 is "2:00". Although the time units are not specified on this screen since they are not strictly necessary, the units could also be displayed for the user or even changed by the user. The entered average speed 116 shown in FIG. 2 is "20 km/u", meaning 20 kilometers per unit time. Based on these two entered values, an estimated distance 118 is calculated to be 40 km, meaning that the user would like to generate an exercise route that is 40 kilometers in length.

Figure 3:
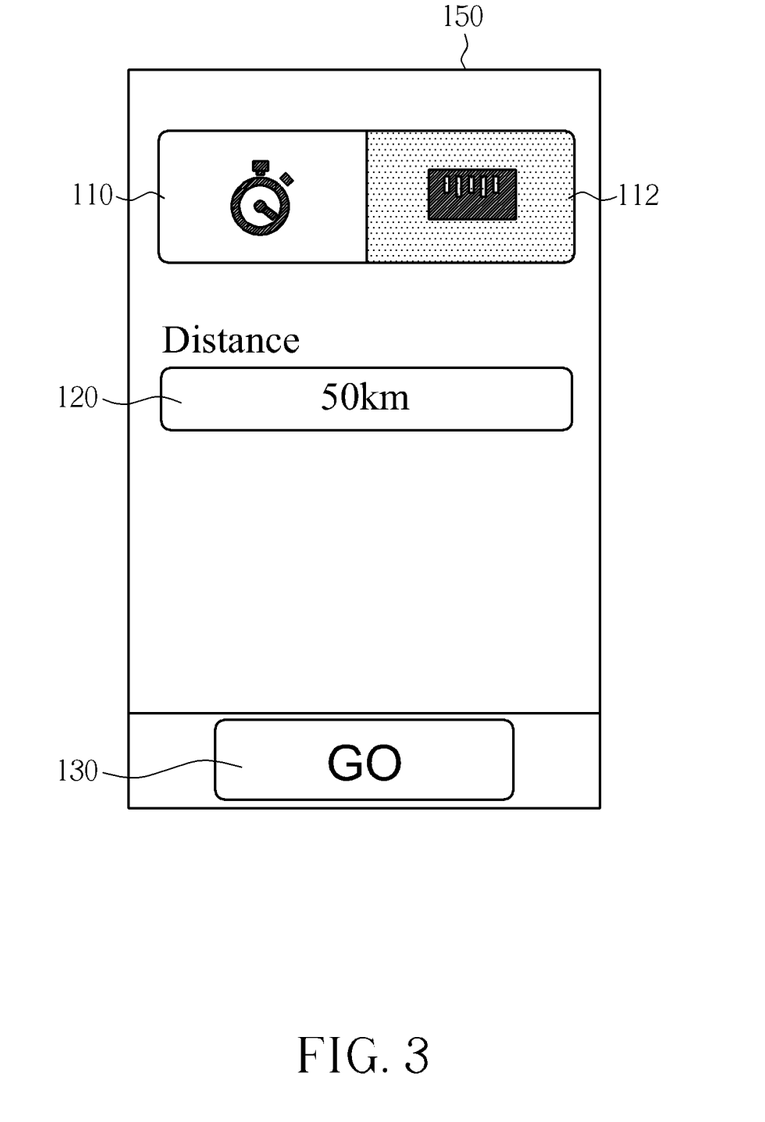
FIG. 3 is a screen showing settings for creating suggested exercise routes with the surprise me function using a distance that the user will travel while exercising.

Please refer to FIG. 2 and FIG. 3. FIG. 3 is a screen 150 showing settings for creating suggested exercise routes with the surprise me function using a distance that the user will travel while exercising. If the user prefers not to input the route length in terms of the entered exercise time 114 and the entered average speed 116, the user can instead press a distance button 112 for indicating the route length in terms of an entered distance 120. For instance, the entered distance 120 shown in FIG. 2 is "50 km", meaning that the user would like to generate an exercise route that is 50 kilometers in length. After the user has input a combination of the entered exercise time 114 and the entered average speed 116 or has input the entered exercise time 114, the user can press a "GO" button 130 for indicating that the user has finished indicating the length of the desired exercise route.

Figure 4:
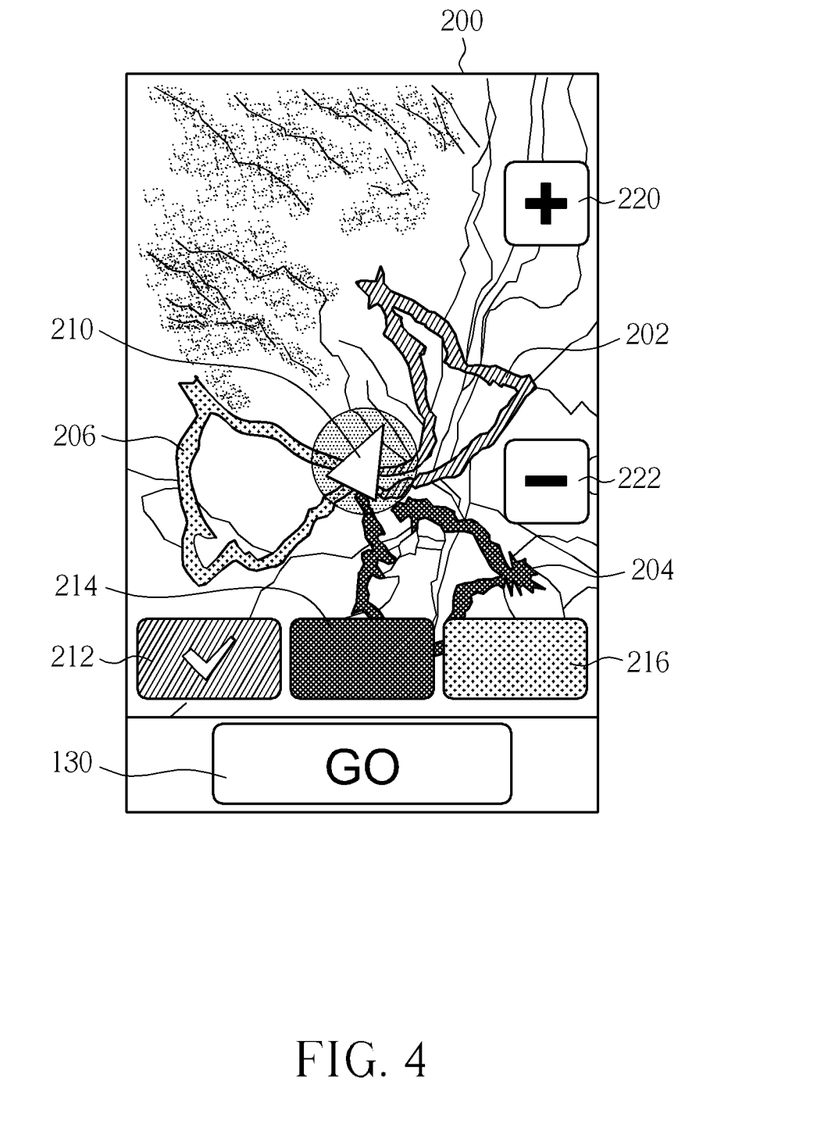
FIG. 4 is a screen showing a map containing three suggested exercise routes displayed on the map.

Please refer to FIG. 4. FIG. 4 is a screen 200 showing a map containing three suggested exercise routes 202, 204, 206 displayed on the map. After the user presses the "GO" button 130 in either FIG. 2 or FIG. 3, screen 200 is shown in the user interface 20 of the personal navigation device 10. Each of the three suggested exercise routes 202, 204, 206 is approximately equal to the length of the exercise route that was previously entered by the user. The three suggested exercise routes 202, 204, 206 preferably all have a starting point and an ending point equal or approximately equal to a current position 210 of the personal navigation device 10, although one-way routes from a starting point to a different ending point could also be used. As shown on screen 200, the current position 210 of the personal navigation device 10 is indicated by a triangle. Other indications for the user's current position 210 besides the triangle can also be used. Once the user has viewed the three suggested exercise routes 202, 204, 206, the user can select one of the three suggested exercise routes 202, 204, 206 by checking one of the corresponding selection boxes 212, 214, 216. In an embodiment, the selection boxes 212, 214, 216 can also contain the exact distance of the corresponding suggested exercise routes 202, 204, 206. A summary of the suggested exercise routes 202, 204, and 206 can also be provided including height profiles, maximum slopes, average slopes, points of interest on the routes, and so on. For example, as shown in FIG. 4, the selection box 212 is checked, meaning that the user has selected the suggested exercise route 202. Once the user has made a selection the user may press the "GO" button 130 to confirm this selection.

If the user does not wish to select any of the three suggested exercise routes 202, 204, 206, the user can simply press a back button on the user interface 20 in order to return to a previous screen such as the screen 100 or the screen 150. At that point the "GO" button 130 can be pressed again to generate another new set of three suggested exercise routes. Other methods can also be used to obtain another set of new suggested exercise routes, including pressing a dedicated button for requesting new exercise routes to be generated. In order to ensure a variety of exercise routes, the present invention strives to present the user with different exercise routes each time the user requests a new set of suggested exercise routes for creating an unlimited number of exercise routes for the user.

The user can zoom in or out of the map shown on screen 200 using a zoom-in button 220 or a zoom-out button 222 in order to get a better idea of where the suggested exercise routes 202, 204, 206 lead. Besides zooming, the user can also pan left and right or up and down. If the display 12 is a touch screen then, the zoom and pan functions can be controlled using the touch screen. While screen 200 shows three suggested exercise routes 202, 204, 206 that have been generated, any number of suggested exercise routes can be generated, including one, two, three, four, or more suggested exercise routes. As long as there are two or more suggested exercise routes, the user will have the ability to select a suggested exercise route that the user prefers from those suggested exercise routes that are displayed at one time.

Figure 5:
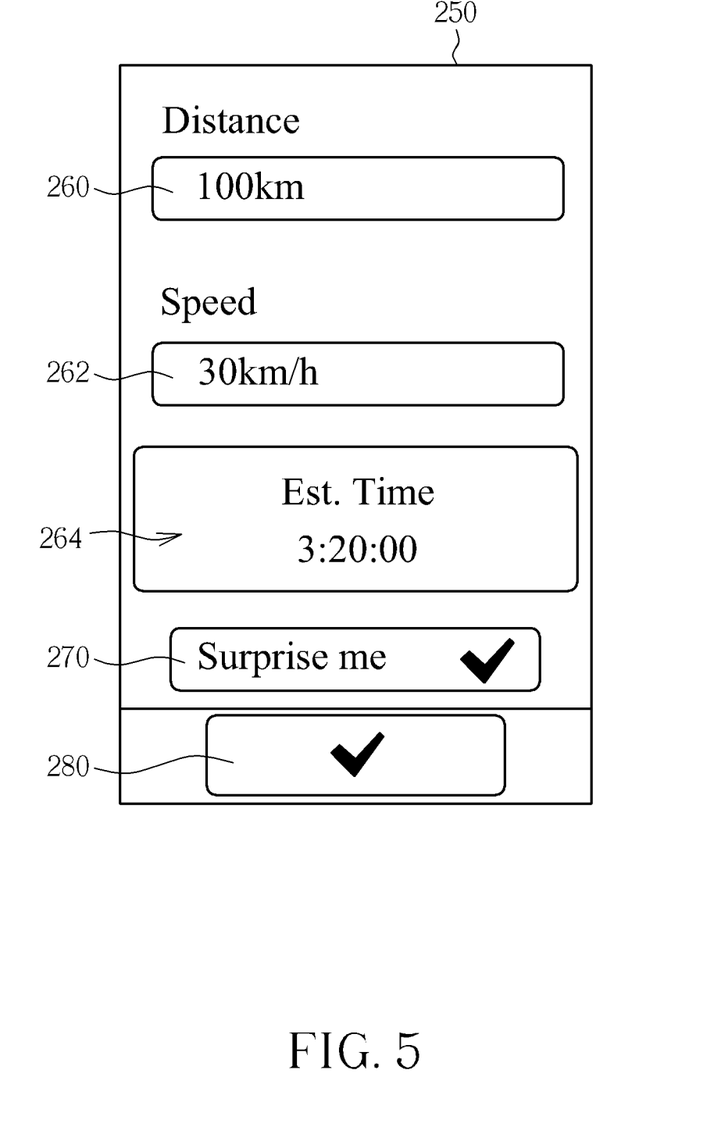
FIG. 5 depicts a workout screen for allowing the user to enter parameters for a desired workout using a combination of distance that the user will travel while exercising and average speed at which the user will move while exercising.

Please refer to FIG. 5. FIG. 5 depicts a workout screen 250 for allowing the user to enter parameters for a desired workout using a combination of distance that the user will travel while exercising and average speed at which the user will move while exercising. The user can then enter the workout length using an entered distance 260 and an entered speed 262. The entered distance 260 shown in FIG. 5 is "100 km", meaning a total length of 100 kilometers. The entered speed 262 shown in FIG. 5 is "30 km/h", meaning the user wishes to travel at an average speed of 30 kilometers per hour. Based on these two entered values, an estimated workout time 264 is calculated to be "3:20:00", meaning 3 hours and 20 minutes. When entering the workout parameters, the user can toggle a surprise me button 270 for correspondingly enabling or disabling the surprise me function for automatically generating suggested exercise routes. Once all workout parameters have been entered, the user can confirm this selection by pressing a confirm button 280. When the user uses the workout screen 250 to generate a workout while enabling the surprise me function for automatically generating suggested exercise routes, the user can be taken to screen 200 shown in FIG. 4 upon pressing the confirm button 280 in FIG. 5.

Figure 6:
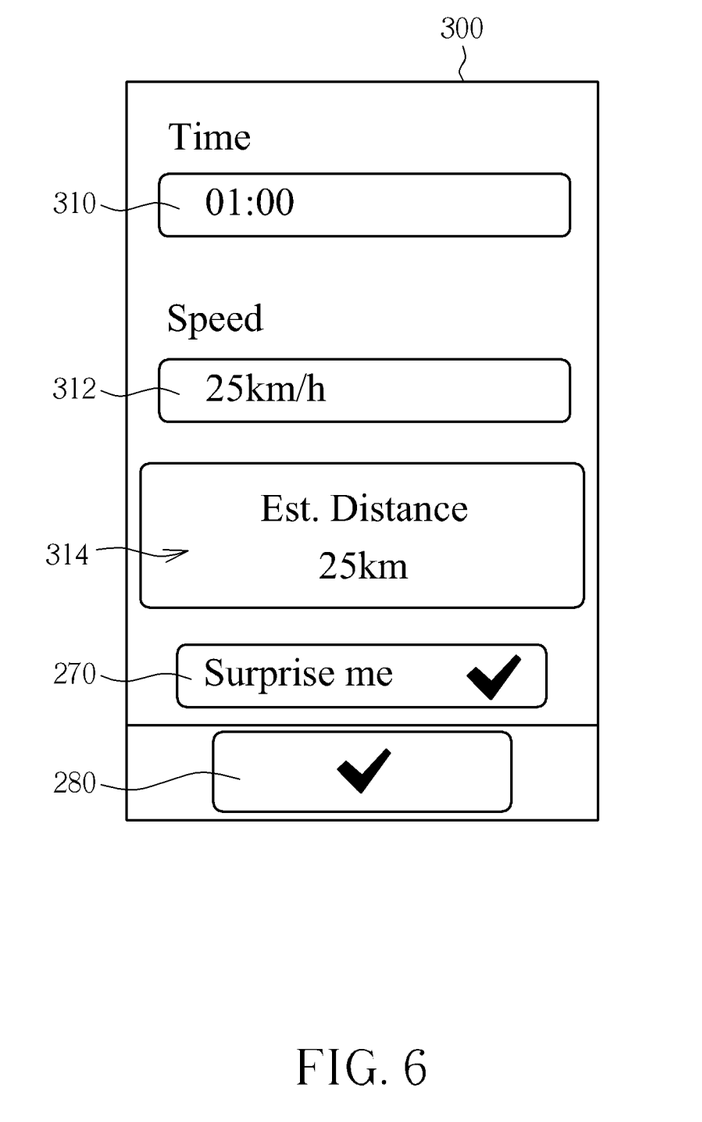
FIG. 6 depicts a workout screen for allowing the user to enter parameters for a desired workout using a combination of exercise time and average speed at which the user will move while exercising.

Please refer to FIG. 6. FIG. 6 depicts a workout screen 300 for allowing the user to enter parameters for a desired workout using a combination of exercise time and average speed at which the user will move while exercising. The user can then enter the workout length using an entered time 310 and an entered speed 312. The entered time 310 shown in FIG. 6 is "01:00", meaning a total exercise time of one hour. The entered speed 312 shown in FIG. 6 is "25 km/h", meaning the user wishes to travel at an average speed of 25 kilometers per hour. Based on these two entered values, an estimated workout distance 314 is calculated to be "25 km", meaning the user will travel over approximately 25 kilometers during the workout. When entering the workout parameters, the user can toggle the surprise me button 270 for correspondingly enabling or disabling the surprise me function. Once all workout parameters have been entered, the user confirms this selection by pressing the confirm button 280. When the user uses the workout screen 300 to generate a workout while enabling the surprise me function for automatically generating suggested exercise routes, the user can be taken to screen 200 shown in FIG. 4 upon pressing the confirm button 280 in FIG. 6.

Numbers entered by the user in any of the previous screens 100, 150, 210, and 300 can be remembered by the personal navigation device 10 so that the user does not need to re-enter the exercise time, average exercise speed, or exercise distance every time a new workout is created. The user will still have the ability to modify these values, but if the user does not wish to make any changes the user can quickly confirm the selection since the numbers will be automatically filled in.

Figure 7:
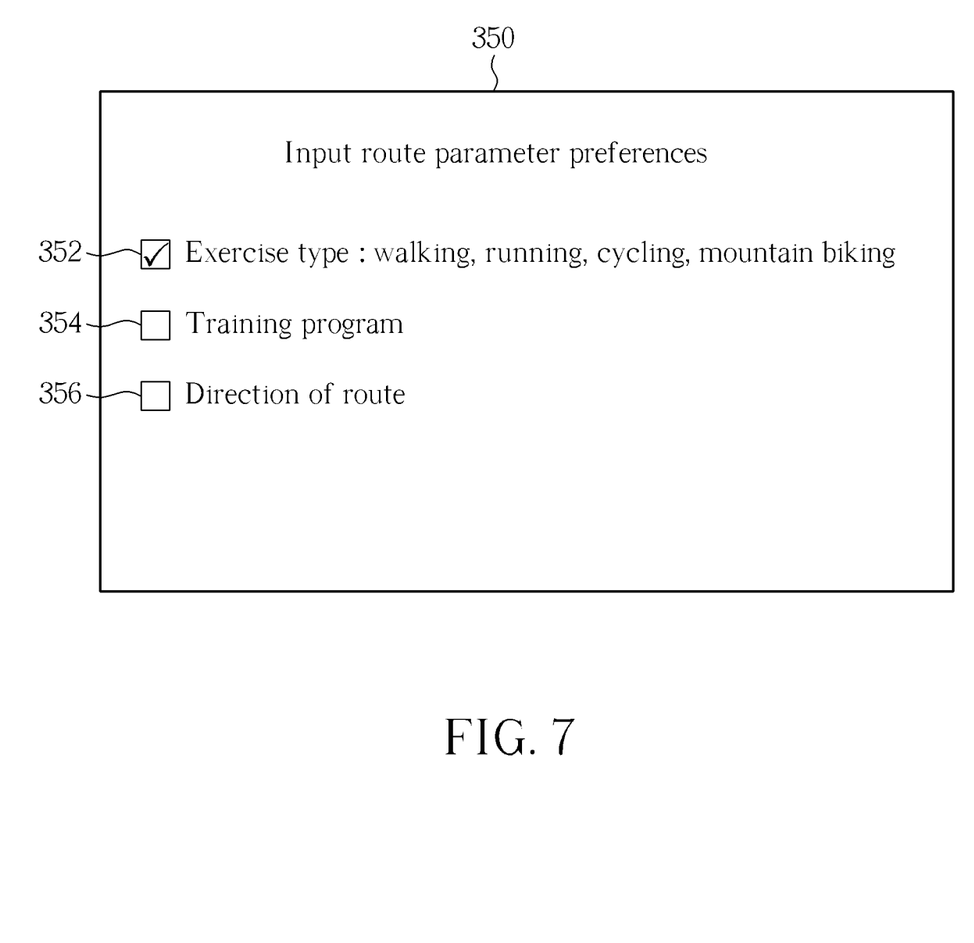
FIG. 7 is a screen showing input route parameter preferences selectable by the user.

The user can select a variety of input route parameters, each of which is further customizable. Please refer to FIG. 7. FIG. 7 is a screen 350 showing an example of input route parameter preferences selectable by the user. When creating an exercise route, the user may select one or more input route parameter preferences for customizing the type of route the user prefers. In screen 350, checkboxes 352, 354, 356 are shown by way of example. Checkbox 352 has been selected for illustrating which input route parameter preferences are selected by the user when creating a new exercise route. In each case, when one of the input route parameter preferences is selected by the user, the user can be presented with an additional screen corresponding to each individual input route parameter preferences for specifying more detail about the user's input route parameter preferences. A description of each of the input route parameter preferences will be given below.

The exercise type 352 option presents the user with the chance to select one of several different types of exercise. Different exercise types such as walking, running, cycling, and mountain biking can potentially all be done on different types of terrain, with the terrain types and attributes can be stored in the map database 32. Different types of biking can also be specified besides mountain bike and cycling, such as a city bike, a race bike, an electric bicycle or a motorbike. By specifying the exercise type 352, the personal navigation device 10 can limit the search for a suitable exercise route to only those that are appropriate for the chosen exercise type 352.

The training program 354 option allows the user to create exercise routes that are consistent with an existing training program that the user is already following and has been entered into the exercise data and preferences 36 portion of memory 30. Using the training program, the user of the personal navigation device 10 receives instructions, suggestions, and motivational encouragement from the personal navigation device 10. Based on the results of previous exercise routes that the user has completed, the training program 354 can create an appropriate exercise route for the user on a given day. Depending on the training program used, the distances of the suggested exercise routes can be increased gradually over time so that the user progressively builds stamina with each workout.

The direction of route 356 option allows the user to either avoid or use certain geographical directions when the routing software 34 generates the suggested exercise routes. For instance the user may have a reason for selecting or avoiding a certain geographical direction when exercising, such as a strong wind blowing out of a certain direction. If the wind is blowing out of the north, the user may wish to travel on an exercise route that travels only east and west, thereby avoiding travel towards the north. Alternatively, the user may wish to start off the exercise route by traveling north so that the user is heading into the wind while the user still has sufficient energy reserves and then return back to the starting point by traveling south with the wind to the user's back. The user can make these selections using the direction of route 356 option.

Besides the input route parameter preferences shown in the screen 350 of FIG. 7, any number of other preferences can be specified by the user such as waypoints to be visited on the exercise route, a direction of a city that the route should head towards, a wind direction to use or avoid, a difficulty level of the exercise route in terms of how flat or steep the exercise route is, heart rate to be achieved by the user on the exercise route, calories to be burned by the user on the exercise route, an expected height or an expected elevation gain of the exercise route, preferred points of interest to be visited on the exercise route, starting and ending points that are different from one other, an unspecified ending point being a specific distance away from the starting point, and surface types such as paved, unpaved, cobblestones, and so on.

In summary, the present invention provides a method of automatically creating a plurality of suggested exercise routes for the user of a personal navigation device to select from in order to provide a more enjoyable and varied exercise experience for the user. The plurality of suggested exercise routes are automatically created for the user based on the user's current location and the length of the exercise route specified by the user. In this way, the user does not need to manually create an exercise route, thereby saving time in planning a route. Further, the user can either select one of the plurality of suggested exercise routes, or the user can request generation of another plurality of suggested exercise routes to choose from. As a result, the user can exercise on an unlimited number of different exercise routes that are enjoyable and challenging, making it more likely that the user will continue exercising for improving fitness. The surprise me function of the present invention will always create a different route so the user can enjoy endless possibilities of exercising.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of creating an exercise route for a user of a personal navigation device, the method comprising:
    storing a database in a memory of the personal navigation device, the database comprising geographic data;
    receiving a selection of a length of an exercise route to be generated;
    generating a first plurality of suggested exercise routes according to a current position of the personal navigation device and the selected length of the exercise route, wherein each of the first plurality of suggested exercise routes has a starting point and ending point substantially equal to one another and equal to the current position of the personal navigation device;
    displaying the first plurality of suggested exercise routes to the user on a display of the personal navigation device, wherein after displaying the first plurality of suggested exercise routes to the user on the display of the personal navigation device the method further comprises:
        receiving a request from the user to generate a second plurality of suggested exercise routes; and
        generating the second plurality of suggested exercise routes according to the current position of the personal navigation device and the selected length of the exercise route in response to receiving the request from the user to generate the second plurality of suggested exercise routes, wherein each of the second plurality of suggested exercise routes has a starting point and ending point substantially equal to one another and equal to the current position of the personal navigation device, and the second plurality of suggested exercise routes are different than the first plurality of exercise routes;
    receiving, from the user, selection of a selected suggested exercise route from the first plurality of suggested exercise routes or the second plurality of suggested exercise routes; and
    displaying routing instructions on the display of the personal navigation device for the selected suggested exercise route.

2. The method of claim 1, wherein the selected length of the exercise route to be generated is indicated by a period of time the user wishes to exercise along with an estimated speed at which the user will travel while exercising.

3. The method of claim 1, wherein the selected length of the exercise route to be generated is indicated by a distance the user wishes to exercise.

4. The method of claim 1 further comprising receiving, from the user, selection of a type of exercise to be performed on the exercise route, wherein generating the first plurality of suggested exercise routes comprises generating the first plurality of suggested exercise routes according to the current position of the personal navigation device, the selected length of the exercise route, and the selected type of exercise.

5. The method of claim 4, wherein the type of exercise to be performed on the exercise route is selected from the group consisting of walking, running, mountain biking, city biking, and race biking.

6. The method of claim 1, wherein generating the first plurality of suggested exercise routes comprises generating three suggested exercise routes and generating the second plurality of suggested exercise routes comprises generating three suggested exercise routes.

7. The method of claim 1 further comprising receiving, from the user, selection of a geographical direction to be considered when generating the first plurality of suggested exercise routes.

8. The method of claim 7, wherein the first plurality of suggested exercise routes are created in order to substantially avoid travel in the selected geographical direction.

9. The method of claim 7, wherein the first plurality of suggested exercise routes are created in order to substantially avoid travel in the selected geographical direction on beginning or ending legs of the first plurality of suggested exercise routes.

10. The method of claim 7, wherein the first plurality of suggested exercise routes are created in order to travel in the selected geographical direction on beginning or ending legs of the first plurality of suggested exercise routes.

11. The method of claim 1 further comprising tracking the user's progress on a training program being followed by the user, and generating the first plurality of suggested exercise routes according to the user's progress on the training program.

12. The method of claim 11, wherein the length of the first plurality of suggested exercise routes is adjusted according to the user's progress on the training program.

13. A personal navigation device for creating an exercise route for a user of the personal navigation device, comprising:
    a memory storing a database comprising geographic data;
    a user interface for receiving from the user a selection of a length of an exercise route to be generated;
    routing software for generating a first plurality of suggested exercise routes according to a current position of the personal navigation device and the selected length of the exercise route, wherein each of the first plurality of suggested exercise routes has a starting point and ending point substantially equal to one another and equal to the current position of the personal navigation device; and a processor for controlling a display of the personal navigation device to display the first plurality of suggested exercise routes to the user, and for controlling the display to display routing instructions for a selected suggested exercise route in response to the user interface receiving from the user selection of the selected suggested exercise route from the first plurality of suggested exercise routes, wherein in response to the user interface receiving a request from the user to generate a second plurality of suggested exercise routes, the routing software generates the second plurality of suggested exercise routes according to the current position of the personal navigation device and the selected length of the exercise route, wherein each of the second plurality of suggested exercise routes has a starting point and ending point substantially equal to one another and equal to the current position of the personal navigation device, and the second plurality of suggested exercise routes are different than the first plurality of exercise routes.

14. The personal navigation device of claim 13, wherein the selected length of the exercise route to be generated is indicated by a period of time the user wishes to exercise along with an estimated speed at which the user will travel while exercising.

15. The personal navigation device of claim 13, wherein the selected length of the exercise route to be generated is indicated by a distance the user wishes to exercise.

16. The personal navigation device of claim 13, wherein the user interface receives from the user selection of a type of exercise to be performed on the exercise route, wherein the routing software generates the first plurality of suggested exercise routes according to the current position of the personal navigation device, the selected length of the exercise route, and the selected type of exercise.

17. The personal navigation device of claim 16, wherein the type of exercise to be performed on the exercise route is selected from the group consisting of walking, running, mountain biking, city biking, and race biking.

18. The personal navigation device of claim 13, wherein generating the first plurality of suggested exercise routes comprises generating three suggested exercise routes and generating the second plurality of suggested exercise routes comprises generating three suggested exercise routes.

19. The personal navigation device of claim 13, wherein the user interface receives from the user selection of a geographical direction to be considered when generating the first plurality of suggested exercise routes.

20. The personal navigation device of claim 19, wherein the first plurality of suggested exercise routes are created in order to substantially avoid travel in the selected geographical direction.

21. The personal navigation device of claim 20, wherein the first plurality of suggested exercise routes are created in order to substantially avoid travel in the selected geographical direction on beginning or ending legs of the first plurality of suggested exercise routes.

22. The personal navigation device of claim 20, wherein the first plurality of suggested exercise routes are created in order to travel in the selected geographical direction on beginning or ending legs of the first plurality of suggested exercise routes.

23. The personal navigation device of claim 13, wherein the processor tracks the user's progress on a training program being followed by the user, and the routing software generates the first plurality of suggested exercise routes according to the user's progress on the training program.

24. The personal navigation device of claim 23, wherein the length of the first plurality of suggested exercise routes is adjusted according to the user's progress on the training program.

* * * * *